United States Patent [19]

Hesse et al.

[11] Patent Number: 4,914,241
[45] Date of Patent: Apr. 3, 1990

[54] PREPARATION OF DIAMINES

[75] Inventors: Michael Hesse, Ludwigshafen; Wolfgang Hoelderich, Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 206,755

[22] Filed: Jun. 15, 1988

[30] Foreign Application Priority Data

Jun. 23, 1987 [DE]  Fed. Rep. of Germany ....... 3720676

[51] Int. Cl.$^4$ .................. C07C 85/18; C07C 87/28; C07C 87/32; C07C 87/48
[52] U.S. Cl. ......................... 564/485; 564/336; 564/373; 564/408; 564/453; 564/455; 564/461; 564/469; 564/474
[58] Field of Search ............... 564/408, 485, 336, 373, 564/453, 455, 461, 469, 474

[56] References Cited

U.S. PATENT DOCUMENTS

| | | | |
|---|---|---|---|
| 2,501,509 | 3/1950 | Gresham et al. | 260/583 |
| 4,375,002 | 2/1983 | Peterson et al. | 564/445 |
| 4,536,602 | 8/1985 | Deeba | 564/485 |

FOREIGN PATENT DOCUMENTS

| | | |
|---|---|---|
| 0039918 | 11/1981 | European Pat. Off. |
| 0077016 | 6/1985 | European Pat. Off. |
| 0101421 | 4/1986 | European Pat. Off. |
| 3326579 | 1/1985 | Fed. Rep. of Germany |
| 3327000 | 7/1985 | Fed. Rep. of Germany |
| 3634247 | 7/1987 | Fed. Rep. of Germany |

*Primary Examiner*—Glennon H. Hollrah
*Assistant Examiner*—Peter G. O'Sullivan
*Attorney, Agent, or Firm*—Keil & Weinkauf

[57] ABSTRACT

Diamines of the formula

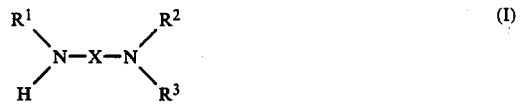

where $R^1$, $R^2$ and $R^3$ are each hydrogen, alkyl, aryl, alkoxy, aralkyl or cycloalkyl and X is a group of the formula

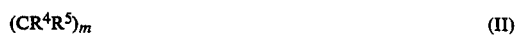

where $R^4$ and $R^5$ have the meanings given above for $R^1$ and m is from 1 to 12, are prepared by a process in which a diamine of the formula

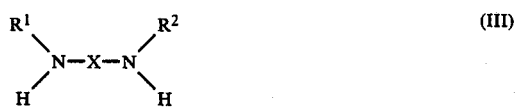

where $R^1$, $R^2$ and X are the groups described above, is reacted with an olefin of the formula

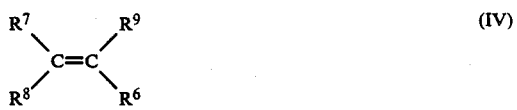

where $R^6$ and $R^9$ are each hydrogen or alkyl which is straight-chain in the α-position, in the presence of a zeolite as a catalyst.

12 Claims, No Drawings

PREPARATION OF DIAMINES

The present invention relates to a process for the preparation of diamines by reacting a diamine with an olefin in the presence of a zeolite as a catalyst.

The N-substitution of diamines by two primary or secondary amino groups, especially of ethylenediamine, is known and can be carried out, for example, by reacting the diamine with an alkyl halide, or with a carbonyl compound under reducing conditions, or by reacting an δ,ω-haloamine with a primary amine or ammonia. However, large amount of N,N-disubstitution products are also obtained. As in the case of the haloamines, the starting materials are not readily available. This makes it more difficult to prepare certain mono-N-alkylated diamines.

The strong acids and their ammonium salts which are obtained in some of the above mentioned processes give rise to serious corrosion problems. Furthermore, the use of halogen-containing compounds is problematic for reasons relating to environmental protection, either because of their toxicity or because of the corrosiveness of the substances liberated, e.g. HI, HBr or their ammonium salts.

It is known that amines can be reacted with olefins, preferably with olefins substituted at the double bond, in the presence of acidic ion exchangers (U.S. Pat. 4,536,602) and in the presence of zeolites to give substituted amines (German Patents 3,326,579 and 3,327,000, U.S. Pat. No. 4,375,002 and European Patents 39,918, 77,016 and 101,921). However, the processes described mention only the addition of NH₃ or monoamines, whereas reactions with diamines are not described.

It is an object of the present invention to provide a process which permits selective substitution of diamines in which there is a possibility of substitution at both N atoms, using catalysts and starting materials which are readily available and not very corrosive.

We have found that this object is achieved and that, surprisingly, the reaction of a diamine with an olefin in the presence of a zeolite as a catalyst gives a good yield of a diamine in which substitution has taken place at only one N atom in the reaction.

The abovementioned N-substituted diamines of the general formula (I)

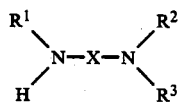
(I)

where $R^1$, $R^2$ and $R^3$ are each hydrogen, alkyl, aryl, alkoxy, aralkyl or cycloalkyl and X is a group of the formula (II)

$$(CR^4R^5)_m \qquad (II)$$

where $R^4$ and $R^5$ have the meanings given above for $R^1$ and m is from 1 to 12, are obtained from a diamine of the formula (III)

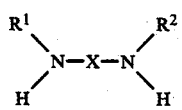
(III)

where $R^1$, $R^2$ and X are each the groups described above for formula (I), and an olefin of the formula (IV)

(IV)

where $R^6$ to $R^9$ are each hydrogen or alkyl which is straightchain in the α-position, in the presence of a zeolite as a catalyst.

This is all the more surprising since disubstitution products are not detectable, despite the presence of excess olefins.

Olefins of the formula (IV) which, according to the invention, can be preferably reacted as starting materials are, for example, ethene, n-propene, n-butene, isobutene, n-pentene, 2-methylbutenes, n-hexene, 2-ethylbutenes, 3-ethylbutenes, n-octene, 2-ethyloctene, nonenes, decenes, cyclopentene, cyclohexene, 1-methylcyclopentene, 1-methylcyclohexene and cyclooctene.

Examples of the di- and polyamines to be reacted according to the invention are ethyldiamine, 1,3-diaminopropane, 1,4-diaminobutane, 1,2-propylenediamine, 2-ethylaminoethylamine, 3-amino-1-methylaminopropane, 3-amino-1-cyclohexylaminopropane, neopentanediamine, hexamethylenediamine, 4,4'-diaminodicyclohexylmethane and 3,3'-dimethyl-4,4'-diaminodiphenylmethane.

The catalysts used for the novel process are zeolites, advantageously in the acidic form. Zeolites are crystalline aluminosilicates which have a highly ordered structure with a rigid three-dimensional network of SiO₄ and AlO₄ tetrahedra which are linked by common oxygen atoms. The ratio of the Si and Al atoms to oxygen is 1:2. The electrovalency of the aluminum-containing tetrahedra is compensated by the inclusion of cations in the crystal, for example an alkali metal or hydrogen ion. Cation exchange is possible. The voids between the tetrahedra are occupied by water molecules prior to dehydration by drying or calcination.

In the zeolites, instead of aluminum, it is also possible for other elements, such as B, Ga, Fe, Cr, V, As, Sb, Bi or Be or a mixture of these, to be incorporated in the framework, or for the silicon to be replaced by a tetravalent element, such as Ge, Ti, Zr or Hf.

Depending on their structure, the zeolites are subdivided into various groups. For example, the zeolite structure is formed by chains of tetrahedra in the mordenite group or by sheets of tetrahedra in the chabasite group, whereas in the faujasite group the tetrahedra are arranged to give polyhedra, for example in the form of a cubooctahedron which is composed of 4-membered rings and 6-membered rings. Depending on the bonding of the cubo-octahedra, resulting in cavities and pores of different sizes, a distinction is made between zeolites of type A, L, X and Y.

Catalysts which are suitable for the novel process are zeolites of the mordenite group or fine-pore zeolites of the erionite or chabasite type or zeolites of the faujasite type, e.g. Y, X or L zeolites.

This group of zeolites also includes the ultrastable zeolites of the faujasite type, ie. zeolites from which aluminum has been removed. Processes for the preparation of such zeolites have been described in many publications.

Zeolites of the pentasil type are particularly advantageous. These possess, as a common building block, a 5-membered ring consisting of SiO$_4$ tetrahedra. They have a high SiO$_2$/Al$_2$O$_3$ ratio and ore sizes which are between those of the zeolites of type A and those of type X or Y.

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, as well as aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably Al(OH)$_3$ or Al$_2$(SO$_4$)$_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali metal or alkaline earth metal, at from 100° to 220° C. under autogenous pressure. These also include the isotactic zeolites according to European Patents 34,727 and 46,504. The aluminosilicate zeolites obtained haven an SiO$_2$/Al$_2$O$_3$ ratio of from 10 to 40,000, depending on the amounts of starting materials chosen. Aluminosilicate zeolites of the pentasil type can also be synthesized in an ether medium, such as diethylene glycol dimethyl ether, in an alcoholic medium, such as methanol or butane-1,4-diol, or in water.

The silicon-rich zeolites (SiO$_2$/Al$_2$O$_3 \geq 10$) which can be used according to the invention also include the various ZSM types, ferrierite, Nu-1 and Silicalite ®.

Borosilicate zeolites can be synthesized, for example, at from 90° to 200° C. under autogenous pressure by reacting a boron compound, e.g. H$_3$BO$_3$, with a silicon compound, preferably finely divided silica, in aqueous amine solution, in particular in 1,6-hexanediamine or 1,3-propanediamine or triethylenetetramine solution, with or, in particular, without the addition of an alkali metal or alkaline earth metal. These also include the isotactic zeolites according to European Patents 34,727 and 46,504. Such borosilicate zeolites can also be prepared if the reaction is carried out in ether solution, eg. diethylene glycol dimethyl ether, or in alcoholic solution, eg. hexane-1,6-diol, instead of in aqueous amine solution.

The iron silicate zeolite is obtained, for example, from an iron compound, preferably Fe$_2$(SO$_4$)$_3$, and a silicon compound, preferably finely divided silica, in aqueous amine solution, in particular hexane-1,6-diamine, with or without the addition of an alkali metal or alkaline earth metal, at from 100° to 200° C. under autogenous pressure.

The aluminosilicate, borosilicate and iron silicate zeolites thus prepared can be isolated, dried at from 100° to 160° C., preferably 110° C., and calcined at from 450° to 550° C., preferably 500° C., and then molded with a binder in a weight ratio of 90:10 to 40:60 to give extrudates or pellets. Suitable binders are various aluminas, preferably boehmite, amorphous aluminosilicates having an SiO$_2$/Al$_2$O$_3$ ratio of from 25:75 to 90:5, preferably 75:25, silica, preferably finely divided SiO$_2$, mixtures of finely divided SiO$_2$ and finely divided Al$_2$O$_3$, TiO$_2$, ZrO$_2$, and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and not subjected to calcination until after the molding procedure. The aluminosilicate and borosilicate zeolites prepared can be used in pure form, without a binder, as extrudates or pellets, the extrusion assistants or peptizing agents used being, for example, ethylcellose, stearic acid, potato starch, formic acid, oxalic acid, acetic acid, nitric acid, ammonia, amines, silicoesters or graphite or a mixture of these. If, because of its method of preparation, the zeolite is present not in the catalytically active, acidic H form but, for example, in the Na form, this form can be completely or partially converted into the desired H form by ion exchange, for example with ammonium ions, followed by calcination, or by treatment with an acid.

In order to achieve very high selectivity, high conversions and long catalyst lives, it is advantageous to modify the zeolites. In a suitable method of modifying the catalysts, for example, the unmolded or molded zeolites are doped with metal salts by ion exchange or by impregnation. The metals used are alkali metals, such as Li, Cs or K, alkaline earth metals, such as Mg, Ca, Sr or Ba, metals of main group 3, 4 or 5, such as B, Al, Ga, Ge, Sn, Pb or Bi, or rare earth metals, such as La, Ce, Pr, Nd, Er, Yb or U. Modification with these metals may be effected by ion exchange or impregnation.

This doping is advantageously carried out as follows: the molded zeolite is initially taken in a riser tube and an aqueous or ammoniacal solution of a halide or of a nitrate of the metals described above is passed over the said zeolite at from 20° to 100° C. Ion exchange of this type can be carried out on the hydrogen, ammonium and alkali metal form of the zeolite. In another possible method for applying the metals to the zeolites, the zeolite materials is impregnated, for example with a halide, a nitrate or an oxide of the metals described above, in aqueous, alcoholic or ammoniacal solution. Both ion exchange and impregnation are followed by one or more drying steps and, if desired, by repeated calcination.

In a possible embodiment, for example, Cu(NO$_3$)$_2$.3-H$_2$O or Ni(NO$_3$)$_2$.6H$_2$O or Ce(NO$_3$)$_3$.6H$_2$O or Cr(NO$_3$)$_3$.6H$_2$O or Pd(NO$_3$)$_2$ is dissolved in water an this solution is used to impregnate the molded or unmolded zeolite for a certain time, eg. 30 minutes. Any supernatant solution is freed from water in a rotary evaporator. Thereafter, the impregnated zeolite is dried at about 150° C. and calcined at about 550° C. This impregnation procedure can be repeated several times in succession in order to obtain the desired metal content.

It is also possible to prepare an aqueous Ni(NO$_3$)$_2$ solution or ammoniacal Pd(NO$_3$)$_2$ solution and to suspend the pure zeolite powder therein at from 40° to 100° C. for about 24 hours while stirring. After the product has been filtered off, dried at about 150° C. and calcined at about 500° C., the zeolite material thus obtained can be further processed with or without a binder to give extrudates, pellets or fluidizable material.

Ion exchange of the zeolite in the H form or ammonium form or alkali metal form can be carried out by a procedure in which the zeolite, in the form of extrudates or pellets, is initially taken in a column and an aqueous Ni(NO$_3$)$_2$ solution or ammoniacal Pd(NO$_3$)$_2$ solution is circulated over the said zeolite at from 30° to 80°

C. for from 15 to 20 hours. Thereafter, the zeolite is washed thoroughly with water, dried at about 150° C. and calcined at about 550° C.

In the case of some metal-doped zeolites, eg., Pd-, Cu- or Ni-doped zeolites, aftertreatment with hydrogen is advantageous.

In another possible method of modification, the molded or unmolded zeolite materials is subjected to a treatment with acid such as hydrochloric acid, hydrofluoric acid and phosphoric acid, and/or steam.

Specifically, an advantageous procedure comprises treating the zeolites in powder form with 1N phosphoric acid for 1 hour at 80° C. After the treatment, the product is washed with water, dried at 110° C. for 16 hours and calcined at 500° C. for 20 hours. In another procedure, zeolites are treated, before or after they have been molded with a binder, with a 3–25, in particular 12–20, % strength by weight aqueous hydrochloric acid, for example for from 1 to 3 hours at 60° to 80° C. The zeolite thus treated is then washed with water, dried, and calcined at from 400° to 500° C.

In a particular embodiment of the acid treatment, the zeolite material, before it has been molded, is treated at elevated temperatures with hydrofluoric acid, which in general is used in the form of 0.001–2N, preferably 0.05–0.5N, hydrofluoric acid, for example by refluxing for from 0.5 to 5, preferably from 1 to 3, hours. After the zeolite material has been isolated by filtering it off and washing it thoroughly, it is advantageously dried at from 100° to 160° C. and calcined at from 450° to 600° C. In another preferred embodiment of the acid treatment, the zeolite material is molded with a binder and then preferably treated with from 12 to 20% strength by weight hydrochloric acid at elevated temperatures, advantageously from 50° to 90° C., preferably from 60° to 80° C., for from 0.5 to 5 hours. The zeolite material can then be washed thoroughly, dried at from 100° to 160° C. and calcined at from 450° to 600° C. An HF treatment can also be followed by a HCl treatment.

In another procedure, zeolites can be modified by applying phosphorus compounds, such as trimethoxyphosphate, trimethoxyphosphine or primary, secondary or tertiary sodium phosphate. Treatment with primary sodium phosphate has proven particularly advantageous. In this procedure, the zeolites in the form of extrudates, pellets or fluidizable material are impregnated with aqueous $NaH_2PO_4$ solution, dried at 110° C. and calcined at 500° C.

If, when the zeolite catalysts are used according to the invention, deactivation occurs as a result of coking, it is advisable to regenerate these catalysts by burning off the coke deposit with air or with an air/$N_2$ mixture at from 400° to 550° C., preferably 500° C. As a result, the zeolites regain their initial activity.

By precoking, it is possible to adjust the activity of the catalyst to obtain optimum selectivity with respect to the desired reaction product.

The catalysts described here can alternatively be used in the form of 2–4 mm extrudates, pellets of 3–5 mm diameter or chips having particle sizes of from 0.1 to 0.5 mm or as a fluidized catalyst.

The reaction conditions generally chosen for the reaction according to the invention are 50°–500° C., eg. 150°–450° C., in particular 200°–400° C., and a WHSV of from 0.1 to 20, in particular from 1.0 to 10.0, g of educt per g of catalyst per hour.

The reaction is generally carried out under from 50 to 500 bar, in particular from 150 to 350 bar.

The molar ratio of the starting materials diamine/olefin is as a rule from 10:1 to 1:10, preferably from 3:1 to 1:2.

The process is generally carried out batchwise or, preferably, continuously.

Sparingly volatile or solid starting materials can be used in dissolved form, for example in solution in tetrahydrofuran, toluene or petroleum ether. The starting material may furthermore be diluted with such solvents.

After the reaction, the resulting products are isolated from the reaction mixture by a conventional method, for example by distillation or extraction, and if necessary brought to the desired purity by further separation operations; unconverted starting materials can be recycled to the reactor.

EXAMPLE 1 TO 7

The following catalysts are used for the Examples:
Catalyst A

A borosilicate zeolite of the pentasil type is prepared in a hydrothermal synthesis from 640 g of finely divided $SiO_2$, 122 g of $H_2BO_3$ and 8,000 g of an aqueous 1,6-hexanediamine solution (weight ratio of mixture 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$. It is molded with boehmite in a weight ratio of 60:40 to give 2 mm extrudates, which are dried at 110° C. for 16 hours and calcined at 500° C. for 24 hours.
Catalyst B Catalyst B is obtained by impregnating catalyst A with an aqueous $Cr(NO_3)_3$ solution, drying the product at 130° C. for 2 hours and then calcining it at 500° C. for 24 hours. The Cr content is 3.2% by weight.
Catalyst C Catalyst C is prepared in the same way as catalyst B, but is impregnated with an aqueous solution of Ce nitrate instead of Cr nitrate. The Ce content is 7.1% by weight.
Catalyst D Catalyst D is prepared similarly to catalyst B but is impregnated with an aqueous solution of Pb nitrate instead of Cr nitrate. The Pb content is 1.2% by weight.

EXAMPLES 1 AND 2

10 ml of the catalyst A described above and 10 ml of the diamine are introduced in a 0.3 l stirred autoclave. The autoclave is closed and the olefins, where they are gaseous, are forced in; otherwise they are introduced together with the diamine. The amount of starting material is chosen so that, at the selected reaction temperature, the desired pressure is obtained in the form of autogenous pressure. If this is not possible, the desired pressure is obtained by means of nitrogen.

EXAMPLES 3 TO 7

The reaction is carried out under isothermal conditions in a tube reactor (coil, 0.6 cm internal diameter, 90 cm length) for not less than 6 hours. The reaction products are isolated and characterized by conventional methods. Quantitative determination of the reaction products and of the starting materials is carried out by gas chromatography.

TABLE 1

| Example | Catalyst | Temperature °C. | Pressure (bar) | Molar ratio EDA/IBU** | Yield of TBEDA* in % of theory (based on EDA) |
|---|---|---|---|---|---|
| 1 | C | 300 | 300 | ½ | 8.6 |
| 2 | C | 300 | 300 | ½ | 9.3 |
| 3 | A | 300 | 300 | ½ | 14.0 |
| 4 | A | 300 | 300 | 1/5 | 5.9 |
| 5 | B | 300 | 300 | ½ | 11.2 |
| 6 | B | 300 | 300 | 1/5 | 20.5 |
| 7 | D | 300 | 300 | ½ | 11.1 |

*TBEDA = N-tert-butylethylenediamine

**IBU = isobutene; EDA = ethylenediamine

We claim:

1. A process for the preparation of a diamine of the formula (I)

$$R^1\!\!\diagdown_{\!\!\!\!\!\!\!\!\!\!\!\!N\!-\!X\!-\!N}\diagup\!\!\!{R^2} \atop H\diagup\qquad\qquad\diagdown R^3 \qquad (I)$$

where $R^1$ and $R^2$ are each hydrogen, alkyl, aryl, aralkyl or cycloalkyl, $R^3$ is alkyl, aryl, aralkyl or cycloalkyl and X is a group of the formula (II)

$$(CR^4R^5)_m \qquad (II)$$

where $R^4$ and $R^5$ have the meanings given above for $R^1$ and m is from 1 to 12, which comprises; reacting a diamine, of the formula (III)

$$R^1\!\!\diagdown_{\!\!\!\!\!\!\!\!\!\!\!\!N\!-\!X\!-\!N}\diagup\!\!\!{R^2} \atop H\diagup\qquad\qquad\diagdown R^3 \qquad (III)$$

where $R^1$, $R^2$ and X are the groups described above for formula (I), with an olefin, of the formula (IV)

$$R^7\!\!\diagdown_{\!\!\!\!\!\!\!\!\!\!\!\!C\!=\!C}\diagup\!\!\!{R^9} \atop R^8\diagup\qquad\quad\diagdown R^6 \qquad (IV)$$

where $R^6$ to $R^9$ are each hydrogen or alkyl which is straight-chain in the α-position, in the presence of a zeolite as a catalyst.

2. The process of claim 1, wherein the diamine of formula (III) is ethylene diamine or propylenediamine.

3. The process of claim 1, wherein the catalyst used is a zeolite of the pentasil type.

4. The process of claim 1, wherein the catalyst used is an aluminosilicate zeolite of the pentasil type.

5. The process of claim 1, wherein the catalyst used is a borosilicate zeolite of the pentasil type.

6. The process of claim 1, wherein the catalyst used is an iron silicate zeolite of the pentasil type.

7. The process of claim 1, wherein the catalyst used is an aluminosilicate zeolite of the faujasite type.

8. The process of claim 1, wherein the catalyst used is an aluminosilicate zeolite of the erionite or offretite type.

9. The process of claim 1, wherein a zeolite catalyst which has been doped with a transition metal and/or noble metal and/or rare earth metal is used.

10. The process of claim 1, wherein a catalyst which has been doped with alkali metals and/or alkaline earth metals is used.

11. The process of claim 1, wherein from 0.05 to 7 moles of olefin are used per mole of amine.

12. The process of claim 1, wherein the diamine of formula (III) is ethylenediamine.

* * * * *